(12) United States Patent
Joergensen et al.

(10) Patent No.: US 6,428,981 B1
(45) Date of Patent: Aug. 6, 2002

(54) BACILLUS PROTEIN PRODUCTION CELL

(75) Inventors: Steen Troels Joergensen, Allerod;
Christina Lund Christensen,
Vaerloese; Tina Kristensen, Hvidovre,
all of (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 09/542,749

(22) Filed: Apr. 4, 2000

Related U.S. Application Data

(60) Provisional application No. 60/130,194, filed on Apr. 20, 1999.

(30) Foreign Application Priority Data

Apr. 16, 1999 (DK) .............................................. 00506/99

(51) Int. Cl.$^7$ ........................... C12P 21/06; C12N 9/00;
C12N 1/20; C12N 15/00
(52) U.S. Cl. ................... 435/69.1; 435/183; 435/252.3;
435/320.1
(58) Field of Search ............................... 435/69.1, 183,
435/320, 252-3

(56) References Cited

PUBLICATIONS

Fuma et al., Nucleic Acids Research, vol. 21, No. 1, pp. 93–97 (1993).
Krause et al., Journal of Bacteriology, vol. 170, No. 10, pp. 4669–4674 (Oct.1988).
Kong et al., Molecular Microbiology, vol. 9, No. 2, pp. 365–373 (1993).
Pang et al., Journal of Bacteriology, vol. 173, No. 1, pp. 46–54 (Jan. 1991).
Guo et al., Biochimica et Biophsica Acta, vol. 1389, pp. 34–42 (1998).
Ryffel et al., Elsevier Science Publishers B.V., Gene, vol. 94, pp. 137–138 (1990).
Cole et al, Nature, vol. 396, pp. 190–544 (Nov. 12, 1998) and Table 1 attachment (5 pages).
Lindum et al., Journal of Bacteriology, vol. 180, No. 23, pp. 6384–6388 (Dec. 1998).
Carlson et al., FEMS Microbioliogy Letters, vol. 151, pp. 225–230 (1997).
Tam et al., Mol. Gen. Genet. vol. 258, pp. 427–430 (1998).
Kunst et al., Nature, vol. 390, pp. 249–256 (Nov. 20, 1997) and Table 1 attachment (5 pages).
Blattner F.R., et al., Abstract of "Analysis of the *Escherichia coli* Genome. IV. DNA sequence of the region from 89.2 to 92.8 minutes."

*Primary Examiner*—Ponnathapu Achutamurthy
*Assistant Examiner*—Manjunath N. Rao
(74) *Attorney, Agent, or Firm*—Elias Lambiris

(57) ABSTRACT

A Bacillus cell for improved production of a polypeptide of interest and a process for producing a polypeptide of interest are disclosed.

36 Claims, No Drawings

BACILLUS PROTEIN PRODUCTION CELL

CROSS-REFERENCE TO RELATED APPLICATIONS

This application claims priority under 35 U.S.C. 119 of U.S. provisional application no. 60/130,194 filed Apr. 20, 1999 and Danish application no. PA 1999 00506 filed Apr. 16, 1999, the contents of which are fully incorporated herein by reference.

BACKGROUND OF THE INVENTION

1. Field of the Invention

The present invention relates to a Bacillus cell for improved production of a polypeptide of interest and a process for producing a polypeptide of interest.

2. Description of the Related Art

Bacillus cells have been widely used for industrial production of polypeptides of interest. Kunst et al., Nature 390: 249–256 (1997) describes the complete genome sequence of the Gram-positive bacterium Bacillus subtilis.

SUMMARY OF INVENTION

The problem to be solved by the present invention is to provide a Bacillus cell capable of producing increased yields of a polypeptide of interest.

The solution is based on that the present inventors have identified that a Bacillus cell expressing less than wild-type level of a gene comprising the DNA sequence shown in SEQ ID NO:1 produces increased yields of a polypeptide of interest.

The gene is identified in a Bacillus subtilis cell and is termed yjbH in the Bacillus subtilis cell. See Kunst et al., Nature 390:249–256 (1997).

Further, the inventors have identified a homologous yjbH gene in a B. licheniformis cell (SEQ ID NO:3).

As stated above (see Background; Kunst et al., Nature 390: 249–256 (1997)) the yjbH gene was, at the priority date of the present invention, NOT annotated, i.e. no known function had been associated with the gene. Based on the teaching provided herein it is among the skilled persons' general knowledge to identify a homologous gene in another Bacillus cell, e.g. by DNA sequence homology to the yjbH genes disclosed herein (SEQ ID NO:1 and SEQ ID NO:3) and thereby readily be able to produce a Bacillus cell capable of producing an increased yield of a polypeptide of interest according to the solution outlined above.

Further, the DNA sequence shown in SEQ ID NO:1 has very low identity to any other known DNA sequences from any cell. A homology search performed in the publicly known databases such as EMBL, showed that no other sequence had any close identity to the DNA sequence shown in SEQ ID NO:1.

Likewise a homology search in the publicly available SWISSPROT database, using the polypeptide sequence shown in SEQ ID NO:2, showed no other polypeptide with any close identity.

Accordingly, in a first aspect the present invention relates to a Bacillus cell for improved production of a polypeptide of interest, wherein the Bacillus cell expresses less than wild-type levels of a gene that comprises:

(a) the DNA sequence shown in positions 1 to 828 in SEQ ID NO:1;

(b) a DNA sequence which is at least 70% identical to the DNA sequence of item (a);

(c) a DNA sequence which encodes a polypeptide sequence shown in positions 1 to 275 in SEQ ID NO:2; or (d) a DNA sequence which encodes a polypeptide sequence which is at least 70% identical to the polypeptide sequence shown in positions 1 to 275 in SEQ ID NO:2.

Further, the present inventors have identified that a partial sequence shown as DNA sequence from position 1 to 147 in SEQ ID NO:1 is highly conserved.

Accordingly, in a second aspect the present invention relates to a Bacillus cell for improved production of a polypeptide of interest, wherein the Bacillus cell expresses smaller than wild-type amounts of a gene that comprises:

(a) the DNA sequence shown in positions 1 to 147 in SEQ ID NO:1;

(b) a DNA sequence which is at least 70% identical to the DNA sequence of item (a);

(c) a DNA sequence which encodes a polypeptide sequence shown in positions 1 to 49 in SEQ ID NO:2; or (d) a DNA sequence which encodes a polypeptide sequence which is at least 70% identical to the polypeptide sequence shown in positions 1 to 49 in SEQ ID NO:2.

As it is clear from the above a Bacillus cell as described herein is highly suitable for the production of a polypeptide of interest.

Accordingly, a third aspect of the present invention is a process for producing a polypeptide of interest comprising the following steps:

(i) cultivating a Bacillus of the first or second preceding aspects under conditions permitting production of the polypeptide of interest;

(ii) isolating the polypeptide of interest.

Definitions

Prior to a discussion of the detailed embodiments of the invention is provided a definition of specific terms related to the main aspects of the invention.

The term "a gene" denotes herein a gene (a DNA sequence) which is capable of being expressed into a polypeptide within said cell. Accordingly, this gene will be defined as an open reading frame starting from a start codon (normally "ATG", "GTG", or "TTG") and ending at a stop codon (normally "TAA", "TAG" or "TGA")).

In order to express the gene there must be elements, as known in the art, in connection with the gene, necessary for expression of the gene within the cell. Such standard elements may include a promoter, a ribosomal binding site, a termination sequence, and may be other elements as known in the art.

The term "the Bacillus cell expresses less than wild-type levels of a gene" according to the first and second aspects of the invention denotes any alterations of the wild-type cell giving rise to a cell which expresses less than wild-type levels of a gene. These alterations may be alterations of a promoter and/or an open reading frame such as deletions, insertions, frame shifts or any manipulations of the DNA as known in the art.

The expression level of a gene in a Bacillus cell altered according to the above is preferably determined by comparing production levels of the polypeptide of interest in said cell with the production level of the polypeptide of interest in the parent non-altered Bacillus cell. If the altered cell produces more of the polypeptide of interest when compared to the non-altered cell, then the Bacillus cell, according to the first and second aspects of the invention, expresses less than wild-type levels of a gene. The actual assay for the determination of production levels of the polypeptide of interest will depend on the specific polypeptide of interest. It is among the skilled persons' general knowledge to choose the appropriate assay.

Identity of DNA Sequences

The DNA sequence identity in relation to the terms "a DNA sequence which is at least 70% identical to the DNA sequence shown in positions 1–828 of SEQ ID NO:1" of the first aspect and "a DNA sequence which is at least 70% identical to the DNA sequence shown in positions 1–147 of SEQ ID NO:1" of the second aspect of the invention is determined as the degree of identity between two sequences indicating a derivation of the first sequence from the second. The identity may suitably be determined by means of computer programs known in the art, such as GAP provided in the GCG program package (Program Manual for the Wisconsin Package, Version 8, August 1994, Genetics Computer Group, 575 Science Drive, Madison, Wis., USA 53711)(Needleman, S. B. and Wunsch, C. D., (1970), Journal of Molecular Biology, 48, 443–453). Using GAP with the following settings for DNA sequence comparison: GAP creation penalty of 5.0 and GAP extension penalty of 0.3, the analogous DNA sequences referred to above exhibits a degree of identity preferably of at least 70%, more preferably at least 75%, more preferably at least 80%, more preferably at least 90%, more preferably at least 95%, more preferably at least 97% with the DNA sequence shown in positions 1–828 of the first aspect of the invention; or the DNA sequence shown in positions 1–147 of SEQ ID NO:1 of the second aspect of the invention.

Identity of Polypeptide Sequences

The polypeptide sequence identity in relation to the terms "a DNA sequence which encodes a polypeptide sequence which is at least 70% identical to the polypeptide sequence shown in positions 1 to 275 in SEQ ID NO:2" of the first aspect and "a DNA sequence which encodes a polypeptide sequence which is at least 70% identical to the polypeptide sequence shown in positions 1 to 49 in SEQ ID NO:2" of the second aspect of the invention is determined as the degree of identity between two sequences indicating a derivation of the first sequence from the second. The homology may suitably be determined by means of computer programs known in the art such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443–453). Using GAP with the following settings for polypeptide sequence comparison: GAP creation penalty of 3.0 and GAP extension penalty of 0.1, the polypeptide encoded by an analogous DNA sequence of the invention exhibits a degree of identity preferably of at least 70%, more preferably at least 75%, more preferably at least 80%, more preferably at least 90%, more preferably at least 95%, and especially at least 97% with the polypeptide sequence shown in positions 1 to 275 of SEQ ID NO:2 of the first aspect, or with the polypeptide sequence shown in positions 1 to 49 of SEQ ID NO:2 of the second aspect of the invention.

Embodiment(s) of the present invention is described below, by way of example(s) only.

DETAILED DESCRIPTION OF THE INVENTION

A Bacillus Cell for Improved Production of a Polypeptide According to the First or Second Aspect of the Invention The gene as described herein is preferably situated between the two well-known genetic markers in Bacillus, srfAA and thyA.

The term "situated between the two well-known genetic markers in Bacillus, srfAA and thyA" denotes herein that the gene is found between the 3'-end of srfAA which is situated at approx. 32° on the *B. subtilis* chromosome, and the 5'-end of thyA which is situated at approx. 162.5° on the *B. subtilis* chromosome (F. Kunst et al., 1997, Nature 390(20): 249–256).

The genetic marker srfAA encodes surfactin synthase sub-unit I in Bacillus, reference is made to (Fuma, S. et al., Nucleic Acids Res. 1993; 21(1): 93–7) for further details.

The genetic marker thyA encodes thymidylate synthases A in Bacillus, reference is made to (Tam, N. H. et al., Mol Gen Genet. 1998; 258(4): 427–30) for further details.

The srfAA marker is a member of a superfamily of homologous markers that are found in numerous different prokaryotic cells, such as swrA in *Serratia liquefaciens* (Lindum et al., J Bacteriol. 1998; 180(23): 6384–8) and grsA in Bacillus brevis (Krause, M. et al., J Bacteriol. 1988; 170(10): 4669–74).

The thyA marker is well known in numerous different prokaryotic cells, such as Neisseria gonorrhoeae (Carlson, J. H. et al., FEMS Microbiol Lett. 1997; 151(2): 225–30), *Bacillus amyloliquefaciens* (Tam, N. H. et al., Mol Gen Genet. 1998; 258(4): 427–30), *Mycobacterium tuberculosis* (Cole, S. T. et al., Nature. 1998; 393(6685): 537–44).

The gene as described herein is more preferably situated between the two well-known genetic markers in Bacillus, mecA and tenA (F. Kunst et al., 1997, Nature 390(20):249–256).

The term "situated between the two well-known genetic markers in Bacillus, mecA and tenA" denotes herein that the gene is found between the 3'-end of mecA which is situated at approx. 105° on the *B. subtilis* chromosome, and the 5'-end of tenA which is situated at approx. 106° on the *B. subtilis* chromosome (F. Kunst et al., 1997, Nature 390(20):249–256).

The genetic marker mecA encodes a negative regulator of genetic competence in Bacillus, reference is made to (Kong, L. et al., Mol Microbiol 1993 July; 9(2): 365–73) for further details.

The genetic marker tenA encodes a polypeptide which regulates production of extracellular enzymes in Bacillus, reference is made to (Pang, A S. et al., J. Bacteriol 1991 January;173(1):46–54) for further details.

These two markers are well known in numerous different prokaryotic cells, such as *Bacillus firmus* (Guo, D. et al., Biochim Biophys Acta Jan. 5, 1998; 1389(1): 34–42), *Staphylococcus aureus* and *S. epidermis* (Ryffel, et al., Gene. Sep. 28, 1990; 94(1): 137–8), *Helicobacter pylori* (Tomb, J F. et al., Nature Aug. 7, 1997; 388(6642):539–47).

Among other based on above-mentioned references it is among the skilled persons' general knowledge to identify these genetic marker genes in a particular Bacillus cell of interest. For example, the specific Bacillus cell may be any Bacillus cell, such as a *Bacillus lentus, Bacillus alkalophilus, Bacillus clausii, Bacillus circulans, Bacillus firmus,* and a *Bacillus thuringiensis* cell.

Preferably, it is a *Bacillus licheniformis, Bacillus subtilis,* or a *Bacillus amyloliquefaciens* cell.

A preferred embodiment of the invention relates to a Bacillus cell as described herein, wherein the Bacillus cell expresses less than wild-type levels of a gene as described herein due to the gene being inactivated.

The gene may be inactivated according to any of the strategies well known to the skilled person, such as deletions, insertions of frame shift mutations within the gene or in the promoter.

A further embodiment relates to a Bacillus cell as described herein, wherein the polypeptide of interest is an enzyme, such as a protease, a cellulase, a lipase, a xylanase, a phospholipase, or preferably an amylase.

In SEQ ID NO:3 and SEQ ID NO:4 is respectively shown the partial DNA and polypeptide sequences of a yjbH gene from *Bacillus licheniformis*. The DNA sequences shown in positions 1 to 147 in SEQ ID NO:1 and the DNA sequence shown in positions 1 to 147 in SEQ ID NO:3 are 76% identical. The polypeptide sequences shown in positions 1 to 49 in SEQ ID NO:2 and the polypeptide sequence shown in positions 1 to 49 in SEQ ID NO:4 are 79% identical.

Accordingly these sequences are within the scopes of the first and second aspects of the invention and an embodiment of the invention then relates to a Bacillus cell wherein the gene comprises the DNA sequence shown in positions 1 to 147 in SEQ ID NO:3 or the gene comprises a DNA sequence encoding the polypeptide sequence shown in positions 1 to 49 in SEQ ID NO:4.

In an even further aspect the present invention relates to a Bacillus cell for improved production of a polypeptide of interest wherein the Bacillus cell expresses smaller than wild-type amounts of a gene that comprises:

(a) the DNA sequence shown in positions 1 to 147 in SEQ ID NO:3;

(b) a DNA sequence which is at least 70% identical to the DNA sequence of item (a);

(c) a DNA sequence which encodes a polypeptide sequence shown in positions 1 to 49 in SEQ ID NO:4; or (d) a DNA sequence which encodes a polypeptide sequence which is at least 70% identical to the polypeptide sequence shown in positions 1 to 49 in SEQ ID NO:4.

All embodiments relating to the first and second aspects of the invention, e.g. preferred homology identities and the situation of the gene between preferred markers are also preferred embodiments in relation to the aspects mentioned immediately above.

A Process for Producing a Polypeptide of Interest Comprising According to the Third Aspect of the Invention An essential element in this process is the use of a Bacillus cell as described herein.

The specific cultivation strategy conditions permitting production of the polypeptide of interest may be any of the numerous cultivation protocols known to the skilled person.

Similarly, the specific strategy for isolating the polypeptide of interest of item ii) of the third aspect may be any of the numerous isolation protocols known to the skilled person.

Further, any range or device value given herein may be extended or altered without losing the effects sought, as will be apparent to the skilled person for an understanding of the teachings herein.

EXAMPLES

Materials and Methods

If not otherwise mentioned, in vitro DNA work, transformation of bacterial cells etc. were performed using standard methods of molecular biology (Maniatis, T., Fritsch, E. F., Sambrook, J. "Molecular Cloning. A laboratory manual". Cold Spring Harbor Laboratories, 1982; Ausubel, F. M., et al. (eds.) "Current Protocols in Molecular Biology". John Wiley and Sons, 1995; Harwood, C. R., and Cutting, S. M. (eds.) "Molecular Biological Methods for Bacillus". John Wiley and Sons, 1990).

If not otherwise mentioned enzymes for DNA manipulations were used according to the specifications of the suppliers.

Media used (TY, BPX and LB agar) have been described in EP 0 506 780. LBPSG agar is LB agar supplemented with phosphate (0.01 M $K_3PO_4$), glucose (0.4%), and starch (0.5%). Agar plates containing dyed amylopectin, as described in WO 94/19454, were used in plate screening for increased amylase production. Minimal medium used was Spizizen's minimal medium in which glucose was replaced by ribose (Spizizen, 1958. Proc. Natl. Acad. Sci. USA 44, 1072–1078).

α-Amylase Assay

α-Amylase activity in culture supernatants was measured using the Phadebas® Amylase Test Kit (Pharmacia Diagnosics). The protocol was provided with the Phadebas assay kit.

Example 1

Inactivation of a Gene Which When Inactivated Gives a *Bacillus subtilis* Cell Capability of Increased Production of an α-amylase:

A *Bacillus subtilis* strain expressing a chimeric α-amylase from a chromosomally integrated gene was mutagenized using the mini-Tn10 transposon pIC333 (Steinmetz, M and Richter, R. 1994, J. Bacteriol. 172: 5019). The strain used was DN1885 xylR::pCJ203, expressing a chimeric α-amylase denoted AmyLQS55-4. The exact composition of this chimeric α-amylase gene and construction of this strain has been published (Christina Lund Jensen (1997) Secretion of chimeric α-amylases from *Bacillus subtilis*. Ph.D. Thesis, Technical University of Denmark (DTU)). Integration of a transposon into the chromosome of *B. subtilis* may result in the inactivation of a target gene; genes, for which such inactivation led to increased amylase production were sought by screening of transposon libraries for increased production of the chimeric α-amylase AmyLQS55-4 by halo formation on LB-plates containing 0.4% glucose, 0.01 M phosphate pH 7, 0.2% xylose, dyed amylopectin, 6 µg/ml Chloramphenicol and 120 µg/ml spectinomycin.

Example 2

Identification of a Gene (SEQ ID NO:1) Which When Inactivated in a *Bacillus subtilis* Cell Renders the Cell Capable of an Increased Production of an α-amylase A Bacillus cell having increased production of the α-amylase was isolated and the identification of a gene (SEQ ID NO:1) was done as described below.

The gene inactivated by the transposon insertion could easily be identified since the mini-Tn10 contained a pUC origin of replication. In order to rescue DNA flanking the transposon insertion, it was necessary to utilize a restriction enzyme which did not cut within the mini-Tn10 transposon. Several restriction enzymes could be used for that purpose; however, in this study, the EcoRI restriction enzyme was used. In most cases, it was possible to obtain the desired plasmids. In addition to the isolation of the flanking regions surrounding the transposon insertions, the chromosomal DNA was also used for Southern blot analysis, in order to check the number of transposon insertions in each mutant. The Southern blot analysis of the transposon mutants using EcoRI restriction enzyme showed that most of the mutants only contained one insertion. Only two of the mutants had more than one transposon inserted in the chromosome.

The flanking regions of the transposon mutants were obtained by digesting the chromosomal DNA with EcoRI followed by ligation and transformation by electroporation into electrocompetent cells of *E. coli* SJ2 (Diderichsen, B. et al. 1990, J. Bacteriol. 172:4315–4321), selecting for spectinomycin resistance (120 μg/ml). The rescued plasmids were checked by restriction enzymes analysis and the gene inactivated by the transposon insertion was identified by sequence analysis of the rescued plasmids using primers TKp1 (5'-CCA ATA CGC AAA CGC CCT CTC-3')(SEQ ID NO:5) and TKp2 (5'-TAG TGA CAT TTG CAT GCT TC-3')(SEQ ID NO:6). DNA sequences were determined by automatic sequencing. In order to identify the genes that were targeted, the obtained sequences were analyzed against the complete genomic sequence of *B. subtilis* (F. Kunst et al., 1997, Nature 390(20): 249–256).

A transposon insertion into the following gene was identified by analyzing a mutant obtained as described in Example 1: yjbH. The transposon insertion was after nucleotide 711 in the yjbH open reading frame.

Example 3

Confirmation That Inactivation of a Gene (SEQ ID NO:1) in a *Bacillus subtilis* Cell Gives Improved Production of an α-amylase Accumulation of α-amylase during prolonged growth in very rich media. The yjbH transposon mutant of strain DN1885 xylR::pCJ203, expressing chimeric α-amylase AmyLQS55-4 from a chromosomal gene copy, was grown in shake flasks and the amount of α-amylase accumulated in the culture supernatant compared to the amount accumulated from the non-mutagenized parent strain. After 7 days fermentation at 37° C. in BPX medium supplemented with 0.2% xylose and 6 μg/ml chloramphenicol the α-amylase activity in the culture supernatants was measured using the Phadebas assay. A 40% increase in the α-amylase activity was observed for the yjbH mutant as compared to the wild-type strain.

Secretion of α-amylase From *B. subtilis* in the Stationary Growth Phase

The yjbH transposon mutant of strain DN1885 xylR::pCJ203, expressing chimeric α-amylase AmyLQS55-4 from a chromosomal gene copy, was also grown in shake flasks containing TY-medium supplemented with 6 μg/ml chloramphenicol and 1% xylose to induce the α-amylase synthesis. During cultivation at 37° C., samples were retrieved to measure the cell density ($OD_{660}$/ml) and the α-amylase activity (NU/ml) in the culture supernatant. The unmutagenized DN1885 xylR::pCJ203 was grown and sampled in parallel. The specific productivity of α-amylase was calculated using the following equation:

$$\text{Specific productivity} = (dP/dt) \times (1/OD_{600})$$

Specific productivity (NU/min/$OD_{660}$)

P: production/activity in culture supernatant (NU/ml)

t: growth time (min)

$OD_{660}$: cell density ($OD_{660}$/ml)

The specific activity is a measure of the capacity of the cell to produce α-amylase within a given time period—in this case within one minute. To calculate the specific productivity, equations describing the growth as a function of time and α-amylase activity as a function of time were estimated from the data points obtained during the growth experiment. These two equations were then used to calculate the specific productivity.

An increase in the specific productivity of α-amylase was observed for the yjbH mutant as compared to the specific productivity of the parent cell. The specific productivity was approximately 70% higher for this mutant as compared to the parent cell in the post-exponential growth phase.

Secretion of α-amylase in the Exponentially Growing *B. subtilis* Cells

The *Bacillus subtilis* strain DN1885 xylR: :pCJ199 (Christina Lund Jensen (1997) Secretion of chimeric α-amylases from *Bacillus subtilis*. Ph.D. Thesis, Technical University of Denmark (DTU)) expresses the wild-type α-amylase of *Bacillus licheniformis* from a chromosomally located gene copy. The yjbH transposon mutation was transferred to this strain by transformation of competent cells of the recipient with chromosomal DNA prepared from the yjbH mutant strain of DN1885 xylR::pCJ203. Selection was for spectinomycin resistance.

The DN1885 xylR: :pCJ199 strain as well as the yjbH mutant derivative were grown in shake flasks using minimal medium containing 1% ribose as the main carbon source supplemented with 6 μg/ml chloramphenicol and 1% xylose for induction of α-amylase synthesis. During the cultivation at 37° C., samples were retrieved for the measuring of the cell density ($OD_{660}$/ml) and the α-amylase activity in the culture supernatant (NU/ml). The specific productivity of α-amylase was calculated as described above.

The specific productivity was approximately 60% higher for the yjbH mutant as compared to the parent cell during exponential growth.

From these data, it is clear that the yjbH mutant is improved with respect to α-amylase production as compared to the wild-type cell.

What is claimed is:

1. A method for producing a polypeptide, which comprises:
   (a) cultivating a mutant of a Bacillus cell, wherein (i) the mutant comprises a nucleic acid sequence encoding the polypeptide, and (ii) the mutant produces less YjbH than the Bacillus cell when cultured under the same conditions, wherein the YjbH (i) is encoded by a DNA sequence that is at least 70% identical to the DNA sequence of nucleotides 1–828 of SEQ ID NO: 11. or (ii) has an amino acid sequence that is at least 70% identical to the sequence of amino acid residues 1–275 of SEQ ID NO: 2; and
   (b) isolating the polypeptide from the culture medium.

2. The method of claim 1, wherein the YjbH has an amino acid sequence that is at least 75% identical to the sequence of amino acid residues 1–275 of SEQ ID NO: 2.

3. The method of claim 2, wherein the YjbH has an amino acid sequence that is at least 80% identical to the sequence of amino acid residues 1–275 of SEQ ID NO: 2.

4. The method of claim 3, wherein the YjbH has an amino acid sequence that is at least 90% identical to the sequence of amino acid residues 1–275 of SEQ ID NO: 2.

5. The method of claim 4, wherein the YjbH has an amino acid sequence that is at least 95% identical to the sequence of amino acid residues 1–275 of SEQ ID NO: 2.

6. The method of claim 5, wherein the YjbH has an amino acid sequence that is at least 97% identical to the sequence of amino acid residues 1–275 of SEQ ID NO: 2.

7. The method of claim 6, wherein the YjbH has an amino acid sequence of amino acid residues 1–275 of SEQ ID NO: 2.

8. The method of claim 7, wherein the YjbH is encoded by the DNA sequence of nucleotides 1–828 of SEQ ID NO: 1.

9. The method of claim 1, wherein the gene encoding the YjbH is located between genetic markers mecA and tenA.

10. The method of claim 1, wherein the Bacillus cell is a *Bacillus amyloliquefaciens, Bacillus licheniformis*, or *Bacillus subtilis* cell.

11. The method of claim 1, wherein the polypeptide is an enzyme selected from the group consisting of amylase, cellulase, lipase, phospholipase, protease, and xylanase.

12. The method of claim 1, wherein the mutant produces no YjbH.

13. A method for producing a polypeptide, which comprises:
   (a) cultivating a mutant of a Bacillus cell, wherein (i) the mutant comprises a nucleic acid sequence encoding the polypeptide, and (ii) the mutant produces less YjbH than the Bacillus cell when cultured under the same conditions, wherein the YjbH (i) is encoded by a DNA sequence that is at least 70% identical to the DNA sequence of-nucleotides 1–147 of SEQ ID NO: 1 or (ii) has an amino acid sequence that is at least 70% identical to the sequence of amino acid residues 1–49 of SEQ ID NO: 2 or (iii) has an amino acid sequence that comprises amino acid residues 1–49 of SEQ ID NO: 2; and (b) isolating the polypeptide from the culture medium.

14. The method of claim 13, wherein the YjbH has an amino acid sequence that is at least 75% identical to the sequence of amino acid residues 1–49 of SEQ ID NO: 2.

15. The method of claim 14, wherein the YjbH has an amino acid sequence that is at least 80% identical to the sequence of amino acid residues 1–49 of SEQ ID NO: 2.

16. The method of claim 15, wherein the YjbH has an amino acid sequence that is at least 90% identical to the sequence of amino acid residues 1–49 of SEQ ID NO: 2.

17. The method of claim 16, wherein the YjbH has an amino acid sequence that is at least 95% identical to the sequence of amino acid residues 1–49 of SEQ ID NO: 2.

18. The method of claim 17, wherein the YjbH has an amino acid sequence that is at least 97% identical to the sequence of amino acid residues 1–49 of SEQ ID NO: 2.

19. The method of claim 18, wherein the YjbH has an amino acid sequence of amino acid residues 1–49 of SEQ ID NO: 2.

20. The method of claim 19, wherein the YjbH is encoded by the DNA sequence of nucleotides 1–147 of SEQ ID NO: 1.

21. The method of claim 13, wherein the gene encoding the YjbH is located between genetic markers mecA and tenA.

22. The method of claim 13, wherein the Bacillus cell is a *Bacillus amyloliquefaciens, Bacillus licheniformis*, or *Bacillus subtilis* cell.

23. The method of claim 13, wherein the polypeptide is an enzyme selected from the group consisting of amylase, cellulase, lipase, phospholipase, protease, and xylanase.

24. The method of claim 13, wherein the mutant produces no YjbH.

25. A method for producing a polypeptide, which comprises:
   (a) cultivating a mutant of a Bacillus cell, wherein (i) the mutant comprises a nucleic acid sequence encoding the polypeptide, and (ii) the mutant produces less YjbH than the Bacillus cell when cultured under the same conditions, wherein the YjbH (i) is encoded by a DNA sequence that is at least 70% identical to the DNA sequence of nucleotides 1–147 of SEQ ID NO: 3 or (ii) has an amino acid sequence that is at least 70% identical to the sequence of amino acid residues 1–49 of SEQ ID NO: 4 or (iii) has an amino acid sequence that comprises amino acid residues 1–49 of SEQ ID NO: 4; and
   (b) isolating the polypeptide from the culture medium.

26. The method of claim 25, wherein the YjbH has an amino acid sequence that is at least 75% identical to the sequence of amino acid residues 1–49 of SEQ ID NO: 4.

27. The method of claim 26, wherein the YjbH has an amino acid sequence that is at least 80% identical to the sequence of amino acid residues 1–49 of SEQ ID NO: 4.

28. The method of claim 27, wherein the YjbH has an amino acid sequence that is at least 90% identical to the sequence of amino acid residues 1–49 of SEQ ID NO: 4.

29. The method of claim 28, wherein the YjbH has an amino acid sequence that is at least 95% identical to the sequence of amino acid residues 1–49 of SEQ ID NO: 4.

30. The method of claim 29, wherein the YjbH has an amino acid sequence that is at least 97% identical to the sequence of amino acid residues 1–49 of SEQ ID NO: 4.

31. The method of claim 30, wherein the YjbH has an amino acid sequence of amino acid residues 1–49 of SEQ ID NO: 4.

32. The method of claim 31, wherein the YjbH is encoded by the DNA sequence of nucleotides 1–147 of SEQ ID NO: 3.

33. The method of claim 25, wherein the gene encoding the YjbH is located between genetic markers mecA and tenA.

34. The method of claim 25, wherein the Bacillus cell is a *Bacillus amyloliquefaciens, Bacillus licheniformis*, or *Bacillus subtilis* cell.

35. The method of claim 25, wherein the polypeptide is an enzyme selected from the group consisting of amylase, cellulase, lipase, phospholipase, protease, and xylanase.

36. The method of claim 25, wherein the mutant produces no YjbH.

* * * * *

SEQUENCE LISTING

<160> NUMBER OF SEQ ID NOS: 6

<210> SEQ ID NO 1
<211> LENGTH: 828
<212> TYPE: DNA
<213> ORGANISM: Bacillus subtilis
<220> FEATURE:
<221> NAME/KEY: CDS
<222> LOCATION: (1)...(828)

<400> SEQUENCE: 1

```
atg ttt gta gac cct tta tgt cct gaa tgc tgg tcc tta gag ccc gtc      48
Met Phe Val Asp Pro Leu Cys Pro Glu Cys Trp Ser Leu Glu Pro Val
```

|  | 1 |  |  | 5 |  |  |  | 10 |  |  |  | 15 |  |  |
|---|---|---|---|---|---|---|---|---|---|---|---|---|---|---|
| atc | aaa | aag | ctg | aaa | atc | aga | tac | gga | cgt | ttt | ttc | acc | tta | cgc | att | 96 |
| Ile | Lys | Lys | Leu | Lys | Ile | Arg | Tyr | Gly | Arg | Phe | Phe | Thr | Leu | Arg | Ile | |
|  |  |  | 20 |  |  |  | 25 |  |  |  |  | 30 |  |  |  |

```
atc gct tcc gca agc ctt acc gct tta aat aaa aag cga aaa aag cat    144
Ile Ala Ser Ala Ser Leu Thr Ala Leu Asn Lys Lys Arg Lys Lys His
         35                  40                  45 ctt ctc gca gaa gca tgg gaa aag atc gcg agc cgc tct ggc atg tca    192
Leu Leu Ala Glu Ala Trp Glu Lys Ile Ala Ser Arg Ser Gly Met Ser
 50                  55                  60 tgt gac ggc aat gtc tgg ttc gaa cag gat cag ccg ctt tca tcg cct    240
Cys Asp Gly Asn Val Trp Phe Glu Gln Asp Gln Pro Leu Ser Ser Pro
 65                  70                  75                  80 tat atg gct gct ctc gct ttt aaa gca gcc gaa ctg caa gga cga aaa    288
Tyr Met Ala Ala Leu Ala Phe Lys Ala Ala Glu Leu Gln Gly Arg Lys
                 85                  90                  95 gcc ggc atg caa ttt ctc aga aat atg cag gag agc cta ttt gtt tca    336
Ala Gly Met Gln Phe Leu Arg Asn Met Gln Glu Ser Leu Phe Val Ser
            100                 105                 110 aag aaa aat att acg gat gaa aac gtg ctt ttg gag att gct gaa aat    384
Lys Lys Asn Ile Thr Asp Glu Asn Val Leu Leu Glu Ile Ala Glu Asn
        115                 120                 125 aca agt ctc gat ctt gaa gaa ttc aaa aaa gat ctg cat tct caa agc    432
Thr Ser Leu Asp Leu Glu Glu Phe Lys Lys Asp Leu His Ser Gln Ser
130                 135                 140 gcg gtc aag gcg ctt caa tgt gac atg aaa att gct gcc gag atg gat    480
Ala Val Lys Ala Leu Gln Cys Asp Met Lys Ile Ala Ala Glu Met Asp
145                 150                 155                 160 gtt tct gtt aat ccg aca ctg acg ttt ttt aat acg cag cat gag gat    528
Val Ser Val Asn Pro Thr Leu Thr Phe Phe Asn Thr Gln His Glu Asp
                165                 170                 175 gaa ggg ctt aaa gtt cct ggc agc tac tca tat gat gta tat gaa gaa    576
Glu Gly Leu Lys Val Pro Gly Ser Tyr Ser Tyr Asp Val Tyr Glu Glu
            180                 185                 190 att tta ttt gag atg ctt ggc gac gag ccg aag ccg tcg gaa aca ccg    624
Ile Leu Phe Glu Met Leu Gly Asp Glu Pro Lys Pro Ser Glu Thr Pro
        195                 200                 205 cct tta gaa tgt ttt att gaa tat ttc cgc ttc gtt gcc tcg aag gaa    672
Pro Leu Glu Cys Phe Ile Glu Tyr Phe Arg Phe Val Ala Ser Lys Glu
    210                 215                 220 att gct ctt gta tat gac ctg agc ctt gaa gag gta gaa aaa gaa atg    720
Ile Ala Leu Val Tyr Asp Leu Ser Leu Glu Glu Val Glu Lys Glu Met
225                 230                 235                 240 aaa aaa ctg gcg ttt gct aaa aag gtt gcc aaa gtg gaa gcc aaa cac    768
Lys Lys Leu Ala Phe Ala Lys Lys Val Ala Lys Val Glu Ala Lys His
                245                 250                 255 gga atg ttt tgg aag tct ctc agc act tat tct gat gaa tat caa tca    816
Gly Met Phe Trp Lys Ser Leu Ser Thr Tyr Ser Asp Glu Tyr Gln Ser
            260                 265                 270 tgt gaa aaa tag                                                    828
Cys Glu Lys  *
        275
```

<210> SEQ ID NO 2
<211> LENGTH: 275
<212> TYPE: PRT
<213> ORGANISM: Bacillus subtilis

<400> SEQUENCE: 2

Met Phe Val Asp Pro Leu Cys Pro Glu Cys Trp Ser Leu Glu Pro Val

```
                1               5                      10                          15
         Ile Lys Lys Leu Lys Ile Arg Tyr Gly Arg Phe Phe Thr Leu Arg Ile
                         20                  25                  30

Ile Ala Ser Ala Ser Leu Thr Ala Leu Asn Lys Arg Lys Lys His
                     35                  40                  45

Leu Leu Ala Glu Ala Trp Glu Lys Ile Ala Ser Arg Ser Gly Met Ser
                 50                  55                  60

Cys Asp Gly Asn Val Trp Phe Glu Gln Asp Gln Pro Leu Ser Ser Pro
         65                  70                  75                  80

Tyr Met Ala Ala Leu Ala Phe Lys Ala Ala Glu Leu Gln Gly Arg Lys
                         85                  90                  95

Ala Gly Met Gln Phe Leu Arg Asn Met Gln Glu Ser Leu Phe Val Ser
                        100                 105                 110

Lys Lys Asn Ile Thr Asp Glu Asn Val Leu Leu Glu Ile Ala Glu Asn
                        115                 120                 125

Thr Ser Leu Asp Leu Glu Glu Phe Lys Lys Asp Leu His Ser Gln Ser
                        130                 135                 140

Ala Val Lys Ala Leu Gln Cys Asp Met Lys Ile Ala Ala Glu Met Asp
         145                 150                 155                 160

Val Ser Val Asn Pro Thr Leu Thr Phe Phe Asn Thr Gln His Glu Asp
                         165                 170                 175

Glu Gly Leu Lys Val Pro Gly Ser Tyr Ser Tyr Asp Val Tyr Glu Glu
                         180                 185                 190

Ile Leu Phe Glu Met Leu Gly Asp Glu Pro Lys Pro Ser Glu Thr Pro
                         195                 200                 205

Pro Leu Glu Cys Phe Ile Glu Tyr Phe Arg Phe Val Ala Ser Lys Glu
                         210                 215                 220

Ile Ala Leu Val Tyr Asp Leu Ser Leu Glu Glu Val Glu Lys Glu Met
         225                 230                 235                 240

Lys Lys Leu Ala Phe Ala Lys Lys Val Ala Lys Val Glu Ala Lys His
                         245                 250                 255

Gly Met Phe Trp Lys Ser Leu Ser Thr Tyr Ser Asp Glu Tyr Gln Ser
                         260                 265                 270

Cys Glu Lys
                 275

<210> SEQ ID NO 3
<211> LENGTH: 149
<212> TYPE: DNA
<213> ORGANISM: Bacillus licheniformis
<220> FEATURE:
<221> NAME/KEY: CDS
<222> LOCATION: (1)...(147)

<400> SEQUENCE: 3 atg ttt gtc gac cct tta tct ccc gaa tgc tgg gca ttg gag ccg gcg        48
Met Phe Val Asp Pro Leu Ser Pro Glu Cys Trp Ala Leu Glu Pro Ala
1               5                  10                  15 atc aaa aag ttg aaa atc cgc tac ggc cgc ttt ttc aca cta agg atc        96
Ile Lys Lys Leu Lys Ile Arg Tyr Gly Arg Phe Phe Thr Leu Arg Ile
                20                  25                  30 atc gcc gca tgc agc att aca gcg ctg aac gtt cag aaa cgc aaa aag      144
Ile Ala Ala Cys Ser Ile Thr Ala Leu Asn Val Gln Lys Arg Lys Lys
            35                  40                  45 cgc cg                                                                149
Arg
```

```
<210> SEQ ID NO 4
<211> LENGTH: 49
<212> TYPE: PRT
<213> ORGANISM: Bacillus licheniformis

<400> SEQUENCE: 4

Met Phe Val Asp Pro Leu Ser Pro Glu Cys Trp Ala Leu Glu Pro Ala
 1               5                  10                  15

Ile Lys Lys Leu Lys Ile Arg Tyr Gly Arg Phe Phe Thr Leu Arg Ile
            20                  25                  30

Ile Ala Ala Cys Ser Ile Thr Ala Leu Asn Val Gln Lys Arg Lys Lys
        35                  40                  45

Arg

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
ccaatacgca aacgccctct c                                         21

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
tagtgacatt tgcatgcttc                                           20
```